(12) United States Patent
Cotton (10) Patent No.: US 10,179,332 B2
(45) Date of Patent: Jan. 15, 2019

(54) FILTRATION DEVICE

(71) Applicant: BRIGHTWAKE LIMITED, Nottinghamshire (GB)

(72) Inventor: Stephen Cotton, Nottingham (GB)

(73) Assignee: Brightwake Limited, Nottinghamshire (GB)

( * ) Notice: Subject to any disclaimer, the term of this patent is extended or adjusted under 35 U.S.C. 154(b) by 332 days.

(21) Appl. No.: 14/755,560

(22) Filed: Jun. 30, 2015

(65) Prior Publication Data

US 2015/0314285 A1 Nov. 5, 2015

Related U.S. Application Data

(63) Continuation-in-part of application No. PCT/GB2014/051843, filed on Jun. 16, 2014.

(30) Foreign Application Priority Data

| Jun. 19, 2013 | (GB) | ................................... | 1310941.8 |
| Oct. 22, 2013 | (GB) | ................................... | 1318671.3 |
| Jun. 16, 2014 | (GB) | ................................... | 1410688.4 |

(51) Int. Cl.
*B01L 3/00* (2006.01)
*G01N 1/40* (2006.01)

(52) U.S. Cl.
CPC ......... *B01L 3/502* (2013.01); *B01L 2200/025* (2013.01); *B01L 2200/026* (2013.01);
(Continued)

(58) Field of Classification Search
CPC .................. B01L 3/502; B01L 2300/12; B01L 2200/0647; B01L 2200/028;
(Continued)

(56) References Cited

U.S. PATENT DOCUMENTS

| 5,240,861 A | 8/1993 | Bieri |
| 5,905,038 A | 5/1999 | Parton |
| (Continued) | | |

FOREIGN PATENT DOCUMENTS

| CN | 2255045 Y | 5/1997 |
| DE | 4237649 A1 | 5/1994 |
| (Continued) | | |

OTHER PUBLICATIONS

Notification of Transmittal, the International Search Report and the Written Opinion of the International Searching Authority, dated Sep. 8, 2014, from the priority International Application No. PCT/GB2014/051843 filed Jun. 16, 2014.
(Continued)

*Primary Examiner* — Sally A Merkling
(74) *Attorney, Agent, or Firm* — Young Basile Hanlon & MacFarlane, P.C.

(57) ABSTRACT

A device for collecting cellular material from a fluid sample comprises first and second chambers that are releasably connected and which define a fluid flow path from the first chamber to the second chamber. A porous membrane is between the chambers when they are connected to each other, in the fluid flow path. An absorbent body is positioned in close proximity to the downstream surface of the porous membrane, and a resilient member is arranged to urge the absorbent body towards the porous membrane. In use, a sample introduced into the first chamber contacts the upstream surface of the porous membrane and fluid is drawn through the porous membrane and is absorbed by the absorbent body. Cellular material is retained upon the upstream surface of the porous membrane. After separation of the chambers, the porous membrane can be removed from the device for analysis of the deposited cellular material.

32 Claims, 7 Drawing Sheets

(52) U.S. Cl.
CPC . *B01L 2200/028* (2013.01); *B01L 2200/0647* (2013.01); *B01L 2300/069* (2013.01); *B01L 2300/0681* (2013.01); *B01L 2300/087* (2013.01); *B01L 2300/12* (2013.01); *B01L 2300/123* (2013.01); *B01L 2400/0406* (2013.01); *G01N 2001/4088* (2013.01)

(58) Field of Classification Search
CPC ......... B01L 2200/026; B01L 2200/025; B01L 2300/069; B01L 2400/0406; B01L 2300/0681; B01L 2300/123; B01L 2300/087; G01N 2001/4088
See application file for complete search history.

(56) References Cited

U.S. PATENT DOCUMENTS

| | | |
|---|---|---|
| 6,358,730 B1 | 3/2002 | Kane |
| 7,546,925 B1 | 6/2009 | Zuk, Jr. |
| 2002/0096468 A1 | 7/2002 | Zuk, Jr. |
| 2002/0110925 A1 | 8/2002 | Mansky et al. |
| 2003/0207466 A1 | 11/2003 | Po Lee |
| 2003/0228705 A1 | 12/2003 | Chan et al. |
| 2006/0254972 A1 | 11/2006 | Tai et al. |
| 2008/0090285 A1* | 4/2008 | Olivier ........................ 435/286.6 |
| 2009/0130766 A1 | 5/2009 | Weekamp |
| 2009/0186341 A1 | 7/2009 | Dahm |
| 2009/0258379 A1 | 10/2009 | Klein et al. |
| 2011/0197685 A1 | 8/2011 | Alburty et al. |
| 2012/0034432 A1* | 2/2012 | Cotton .............. A61F 13/15699 428/195.1 |
| 2012/0164627 A1 | 6/2012 | Battrell et al. |

FOREIGN PATENT DOCUMENTS

| | | |
|---|---|---|
| EP | 0122581 A2 | 10/1984 |
| EP | 0122581 A3 | 7/1987 |
| EP | 0419168 A2 | 3/1991 |
| JP | S63-77502 A | 4/1988 |
| JP | H0792160 A | 4/1995 |
| JP | 3028764 B2 | 4/2000 |
| WO | 9637600 A1 | 11/1996 |
| WO | 9735871 A1 | 10/1997 |
| WO | 2011092201 A1 | 8/2011 |

OTHER PUBLICATIONS

GB Search Report dated Dec. 18, 2013, from Priority Application No. GB 1310914.8.
GB Search Report dated Dec. 11, 2014, from Priority Application No. GB 1410688.4.

* cited by examiner

FILTRATION DEVICE

CROSS REFERENCE TO RELATED APPLICATIONS

This application is a continuation-in-part of International Patent Application PCT/GB2014/051843, filed on Jun. 16, 2014, which claims priority to GB Patent Application serial nos. 1310941.8, filed on Jun. 19, 2013, 1318671.3, filed on Oct. 22, 2013, and 1410688.4 filed on Jun. 16, 2014, each incorporated herein by reference.

TECHNICAL FIELD

The present invention relates to a filtration device. In particular, the present invention relates to a filtration device for use in microbiological filtration, for use in the separation and collection of cells, microbes and/or other microorganisms from a fluid sample.

BACKGROUND

There are many industries in which it is necessary to analyse a liquid sample for the presence of cells, microbes and/or other microorganisms. In particular, quality control in the food and beverage industries commonly requires the analysis of samples of materials such as dairy products, juices, soft drinks, beer, wine and oils for the presence of spoilage organisms, eg microfungi such as yeasts. Regulatory requirements mean that pharmaceutical products and cell cultures are regularly tested for the presence of undesirable microorganisms. Microbiological filtration is also routinely carried out in the testing of potable and waste water, in environmental control and monitoring, in the cosmetics industry, and in the medical field, particularly in diagnostics.

In the medical field, it is often necessary to separate and collect cells from a biological sample in order to enable the cells to be analysed. This may be required, for example, in order to diagnose and/or treat certain diseases. For example, the analysis of cells extracted from a urine sample may be used in the diagnosis of bladder cancer, or the separation of cells from faeces may be used in the diagnosis of cancer of the GI tract.

Conventionally, cells and other microorganisms are collected from fluid samples using a centrifuge, where the forces exerted by a high speed centrifuge cause the larger, denser particles in a sample to sediment out. Typically, the larger particles include cellular material contained within the sample, which has been separated from the fluid component of the sample. Once the cellular material has been obtained, it can be analysed using a microscope or other analytical method.

During the process of centrifugation, the fluid sample and cellular material contained within it are subject to significant forces. These forces can cause damage, such as cell rupture, to the cellular material. This can affect the results which are obtained, and/or may result in it being difficult to reach a conclusion, eg a diagnosis or determination of the microorganisms present, when the extracted material is analysed.

In addition, due to the need for specialist equipment, it is often necessary for the fluid sample to be sent to a remote laboratory in order for centrifugation and analysis to be carried out. This is a particular issue in the analysis of biological samples. Cellular material contained within a biological sample degrades with time, and any time delay between obtaining a sample and analysing it can therefore result in the analysed material becoming damaged. This may affect the results obtained, and/or make it difficult for a conclusion to be reached. The necessity for the use of specialist equipment requiring the sample to be sent to a remote laboratory to be separated and analysed is therefore undesirable, as it introduces delay into the process and so increases the risk of the extracted cells or other microorganisms becoming damaged.

There is thus a need for a method of collecting cells and/or microbiological material from a fluid sample which minimises the damage caused to the collected material, in order to optimise the quality of the extracted cellular and/or microbiological material and so enable accurate determination of the cellular, microbial and/or other microbiological content of the sample to be made.

SUMMARY

There has now been devised an improved filtration device, which overcomes or substantially mitigates the above-mentioned and/or other problems associated with the prior art.

According to a first aspect of the invention there is provided a device for collecting cellular material from a fluid sample, the device comprising:
a) first and second chambers that are releasably connected and which define a fluid flow path from the first chamber to the second chamber;
b) a porous membrane captivated between the first and second chambers when the first and second chambers are connected to each other, the porous membrane being positioned in the fluid flow path and having upstream and downstream surfaces;
c) an absorbent body positioned adjacent to the downstream surface of the porous membrane; and
d) a resilient member arranged to urge the absorbent body towards the porous membrane;
e) wherein, in use, a sample introduced into the first chamber contacts the upstream surface of the porous membrane and fluid is drawn through the porous membrane and is absorbed by the absorbent body, cellular material present in the sample being retained upon the upstream surface of the porous membrane,
f) and wherein, after separation of the first and second chambers, the porous membrane can be removed from the device for analysis of cellular material deposited on the upstream surface thereof.

In order to collect cellular material from a fluid sample using the device of the invention, the sample is introduced into the first chamber, onto the porous membrane. The absorbent body, positioned adjacent to the downstream surface of the porous membrane, draws the fluid from the sample, through the porous membrane. By "adjacent" in this context is meant that the absorbent body is in contact with the porous membrane, or is in sufficiently close proximity to the porous membrane to draw fluid from the sample through the porous membrane. The resilient member maintains the contact or close proximity of the absorbent body and the porous membrane. The resilient member nonetheless permits expansion of the absorbent body as it absorbs fluid from a sample introduced into the first chamber. Cellular material, which cannot pass through the porous membrane, is retained on its upstream surface. The porous membrane may then be removed from the device for analysis of the collected material using a microscope or other suitable analytical technique. If necessary, the porous membrane may be placed in a petri dish with culture media to grow the microorganisms present, prior to analaysis.

By cellular material is meant, in the context of the invention, any material that contains cells, and may include extracted cells, microbes and/or microorganisms.

The fluid sample may be any sample for which it is desirable to carry out microbiological filtration. For example, and without limitation, the fluid sample may be a biological sample, a sample of food or drink, a pharmaceutical sample or pharmaceutical cell culture, a water sample, a wastewater sample, a potable water sample, a cosmetics sample, or other fluid sample taken for the purposes of environmental control and monitoring.

Where the fluid sample is a biological sample, the biological sample may be any sample containing cells which it is desirable to extract. For example, the biological sample may be whole blood, plasma, serum, cerebrospinal fluid, urine, bile, faeces, mucus, amniotic fluid, lymph, pericardial fluid, saliva or synovial fluid.

The filtration device of the present invention is advantageous primarily in that it does not require the use of additional, specialist laboratory equipment such as a centrifuge or vacuum pump. This means that the collection of cellular material can be carried out in situ, without an undue delay between obtaining the sample and carrying out the collection, thus reducing the chance of degradation of the cellular material contained within the sample. Once the cellular material has been collected from the fluid sample, the membrane may be immediately removed from the device and the material analysed using a microscope or other analytical technique. This again reduces the delay between obtaining the fluid sample and analysis of the collected material. In addition, the ability to analyse the cellular material on the removed membrane reduces the need to handle the collected material and consequently reduces the risk of damage. The filtration device of the present invention does not submit the fluid and/or separated cellular material to excess forces (as is the case when a centrifuge is used), again reducing the risk of damaging or rupturing the cellular material before it is analysed. By maintaining the close proximity of the absorbent body with the porous membrane, the resilient member facilitates the passage of fluid through the porous membrane, and hence the collection of cellular material of interest on the porous membrane.

The device of the invention preferably comprises a casing which defines the first and second chambers, and within which the removable porous membrane and absorbent body are contained. For example, the casing may comprise an inlet portion and a base container, the inlet portion defining the first chamber and the base container defining the second chamber, the inlet portion and base container being connectable together. In such a configuration the absorbent body will generally be contained within the base container, and the porous membrane will generally be captivated between the two components.

Where the casing comprises multiple components, eg an inlet portion and a base container, those components may be connected together using any suitable means, and may be detachably attached to each other. For example, the two or more components comprising the casing may be detachably connected together using a screw-type fitting, a bayonet-type fitting, one or more clips, or by an interference fit, to permit separation of the first and second chambers. The components that together constitute the casing are most preferably formed in plastics materials, eg by injection moulding.

The first and second chambers may be any suitable size and shape. For example, either or both chambers may be defined by an open-topped vessel, such as an open-topped cylindrical vessel or an open-topped funnel-shaped vessel. It will be appreciated that the first and second chambers may have a circular cross-section, but may also have any other suitable shape, for example a square cross-section, a pentagonal cross-section, a hexagonal cross-section etc. The second chamber is of suitable volume to capture any fluid which is not retained by the absorbent material, and may typically have a volume of between about 10 and 250 ml, or between about 50 and 250 ml. In other embodiments, the second chamber may be smaller, eg with a volume of between about 15 and 35 ml, or of between about 20 and 30 ml.

For many applications, the device will have overall dimensions comparable to those of a conventional jar or flask used for collection of, for instance, a urine sample. In such cases, the device is typically between about 20 and 100 mm in width. The width of the device may be between about 40 and 80 mm, or between about 40 and 70 mm. The height of the device may be between about 50 and 150 mm, or between about 60 and 140 mm, or between about 70 and 100 mm.

The porous membrane acts as a filter, allowing fluid from the sample to pass through it whilst retaining cellular material on its surface. Suitable materials for such a purpose are known in the art, and any suitable material may be used in the present invention. Preferably, the porous membrane is a membrane filter. Membrane filters typically have a smooth, flat surface, ensuring that cellular material which is retained on the surface of the membrane is easily visible using a microscope or other analytical technique. In addition, membrane filters typically have consistent pore sizes and densities, enabling the correct size of filter to be easily selected in order to retain the desired components from the fluid sample. Different types of membrane filter are known in the art, and the filter may be, for example, a microporous membrane, a track-etched membrane or an ultrafiltration membrane.

The porous membrane may made of any suitable material, and may be polycarbonate, polyester, polyvinylidene fluoride, polyethersulfone, mixed cellulose esters, ultra-high molecular weight polyethylene, nylon polymer and/or PTFE. Preferably, the porous membrane is a polycarbonate membrane.

The pore size of the porous membrane is selected based on the type of material which it is intended to collect on its surface. Hence, a suitable pore size for use in the invention may be selected depending on the material to be collected, but typically corresponds to the size of the smallest particle which is to be retained and analysed. For the retention of cellular material in the present invention, the porous membrane will typically have an average pore size of between about 0.1 and 5 µm.

In order to ensure retention of all viable microorganisms in a sample, a pore size of less than about 0.45 µm, or of between about 0.1 µm and about 0.45 µm, is preferable, and may be particularly suitable where a sample is believed to contain a low number of cells. However, for many applications where the specific retention of larger cells is required (eg in the analysis of a biological sample), larger pore sizes may be appropriate, for example the porous membrane may have an average pore size of between about 0.5 and 4 µm, or of between about 1 and 3 µm.

As the porous membrane itself may be flexible, it is preferable for it to be retained within a holder in order to facilitate handling of the membrane. Such a holder may, for example, take the form of a rigid ring or frame within which the membrane is fixed, and which may be removably inserted into the device. The use of a holder enables easy removal of the porous membrane from the device, reducing or preventing flexion of the membrane as it is transferred from the device for analysis, and thus preventing loss or damage to the cellular material retained on its surface.

When the device is in use, the absorbent body is positioned in close proximity to the downstream surface of the porous membrane. The absorbent body may be in direct contact with the downstream surface of the porous membrane, or an intermediate component, which will necessarily also be porous or otherwise fluid-transmissive, may be interposed between the absorbent body and porous membrane.

In currently preferred embodiments, the absorbent body is housed within a rigid holder that is, in the assembled device, captivated between the components (eg an inlet funnel and a base container) that define the first and second chambers. Such a holder may take the form of a ring or other frame that accommodates the absorbent body. In such cases, the holder may also accommodate a fluid-transmissive cover and/or the resilient member for urging the absorbent body into close proximity with the porous membrane.

The resilient member conveniently takes the form of a compressible body, eg of foam plastics material, that is located beneath the absorbent body and fills the void within the holder, pressing the absorbent body upwards, towards the porous membrane. The compressible body thus acts in the manner of a compression spring. In use, as the absorbent body absorbs fluid from a sample, the absorbent body swells and compresses the compressible body, thereby allowing the swelling of the absorbent body to be accommodated within the holder. The compressible body is therefore preferably easily deformable, to allow for expansion of the absorbent body, and is sufficiently porous to allow excess fluid from the sample to pass through. A particularly suitable material for use as the compressible body is a soft, open-celled plastics foam. Such material may be sponge-like, its open-celled nature permitting the flow of fluid through it and its resilience being sufficient to press the absorbent body towards the porous membrane, but not to substantially impede the expansion of the absorbent body as it absorbs fluid in use.

Alternatively, the resilient member may comprise a sheet of material having a degree of elasticity, such that the sheet of material is sufficiently deformable to accommodate the swelling of the absorbent body whilst at the same time having sufficient resistance to apply a gentle upward pressure to the absorbent body. The sheet of material may be located beneath the absorbent body within the rigid holder. The sheet of material is preferably capable of stretching equally in all directions and is sufficiently porous to allow excess fluid to pass through it. A particularly suitable material is a circular knitted material. Such material is capable of expanding evenly in all directions and is porous. This embodiment is advantageous as a sample with a larger volume of fluid may be used. The fluid can easily pass through the sheet of material and the absorbent assembly in this embodiment takes up less of the void within the second chamber, allowing a greater volume of fluid to be collected in the second chamber.

The absorbent body may comprise any absorbent material which is sufficiently absorbent to retain a quantity of liquid. Preferably, the absorbent material is sufficiently absorbent to actively draw liquid contained within the sample through the membrane. More preferably, the absorbent body comprises a superabsorbent material.

"Superabsorbent material" in the context of the present invention means a material that is capable of absorbing many times its own mass of water, eg up to 200, 400 or 500 times or more its own mass of water.

Although it should be appreciated that the absorbent body may comprise any superabsorbent material, preferred superabsorbent materials are polymeric superabsorbent materials and include alginate, polyacrylate (ie a salt of polyacrylic acid), polyacrylamide copolymers, ethylene maleic anhydride copolymer, carboxymethylcellulose, polyvinylalcohol copolymers, polyethylene oxide and starch-grafted copolymers of polyacrylonitrile.

Many such superabsorbent materials may be used in particulate form. In such cases, the particles may be incorporated into a carrier material, for instance by being encapsulated between two layers of carrier material, eg tissue paper or the like.

Alginate superabsorbent materials may be sodium or calcium alginate. The alginate superabsorbent is preferably in the form of a non-woven mat, providing a superabsorbent layer suitable for the method of the present invention.

The most preferred superabsorbent material is sodium polyacrylate polymer. Sodium polyacrylate polymer is a solid crystalline material, and is preferably incorporated into a sheet in the form of particles encapsulated between two layers of carrier material, such as tissue paper. A specific example of a suitable material is Gelok® 14040S/S manufactured by Gelok International Corporation.

The device of the present invention may additionally comprise a second, cover membrane located between the porous membrane and the absorbent body. The cover membrane is also porous, with a pore size sufficient to allow the unrestricted flow of fluid between the porous membrane and the absorbent body. The pore size of the cover membrane is typically much larger than the pore size of the porous membrane, and may be between 100 µm and 2 mm, for instance between 0.5 and 2 mm. The cover membrane may be a membrane filter as discussed above, or may alternatively be a woven or nonwoven mesh or scrim.

The device of the invention may be supplied in parts to be assembled by the user, but preferably is supplied in its fully assembled configuration. The device may be reusable on replacement of the porous membrane and absorbent body, or may be disposable, being discarded after a single use. Preferably, the device is disposable, removing the need for sterilisation and ensuring that no cross-contamination occurs between samples.

The device described above is used to collect cellular material from a fluid sample for analysis. Hence, according to a second aspect of the invention there is provided a method for collecting and analysing cellular material from a fluid sample, the method comprising:
a) introducing a fluid sample into the device of the first aspect of the invention, such that the sample is in contact with the upstream surface of the porous membrane; and
b) subsequently removing the porous membrane from the device, for analysis of the cellular material deposited on its upstream surface.

It will be appreciated that the device for use in the second aspect of the invention may have any of the features described in relation to the first aspect of the invention.

The method involves filtering the fluid sample for a length of time. Once a length of time has elapsed from introduction of the fluid sample into the device, any remaining fluid which has not been filtered may simply be discarded before the porous membrane is removed for analysis of the cellular material deposited thereon. The appropriate length of time for filtration may be dependent upon the speed of filtration, which is affected by the nature of the sample to be filtered and the pore size of the porous membrane, and the concentration of cellular material in the fluid sample. An appropriate length of time may therefore vary depending on the device and sample, but should be of a sufficient length to allow an analysable quantity of cellular material to accumulate on the upstream surface of the porous membrane.

Alternatively, the sample may be filtered until a suitable volume of fluid has passed through the porous membrane. The volume of fluid to be filtered may comprise the entire sample which is introduced into the device, or a portion of the sample. The volume of fluid may be dependent on the absorption capacity of the absorbent body, the volume of the first and second chambers, and/or the concentration of cellular material in the fluid sample, but should be sufficient to allow an analysable quantity of cellular material to accumulate on the upstream surface of the porous membrane. Where the predetermined volume of fluid comprises a portion of the fluid sample introduced into the device, the unfiltered portion of the sample is discarded prior to removal of the porous membrane and analysis of the cellular material.

DESCRIPTION OF THE DRAWINGS

The invention will now be described in greater detail, by way of example only, with reference to the accompanying drawings, in which.

DETAILED DESCRIPTION

Figure 1:
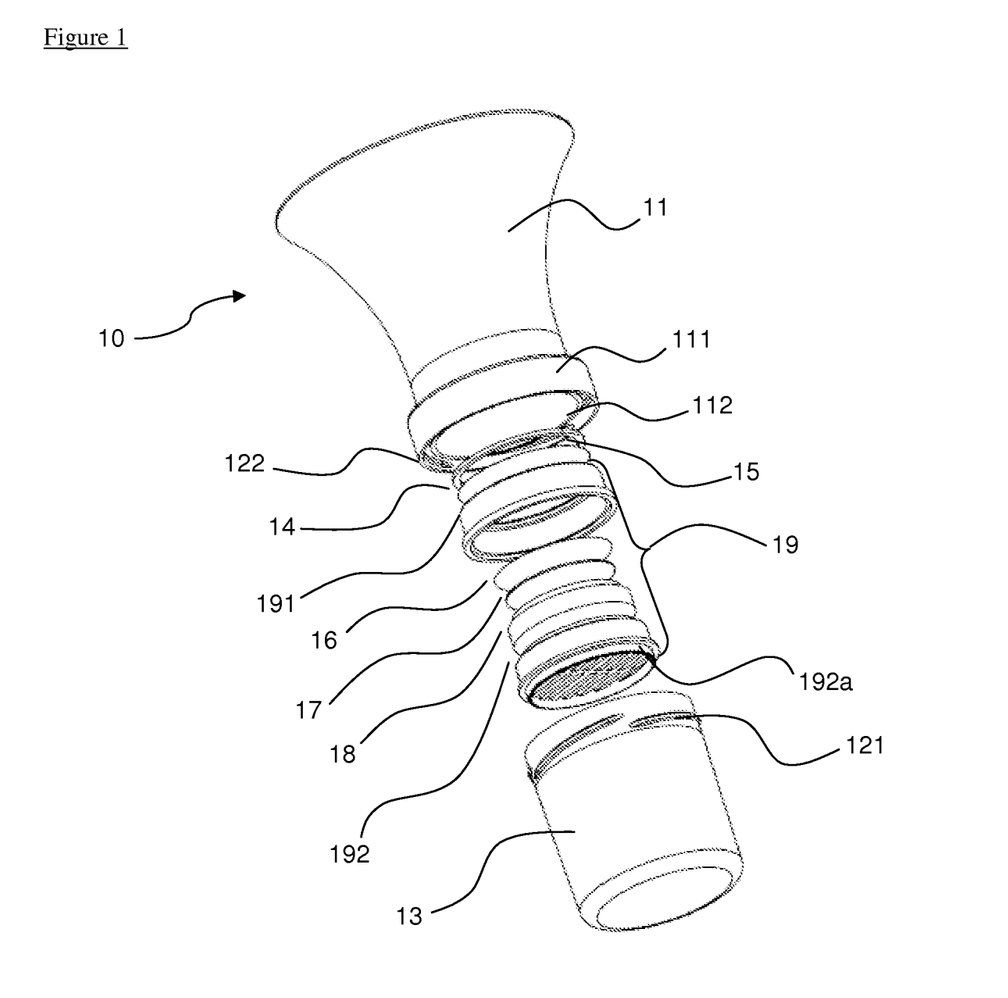
FIG. 1 shows an exploded view of a first embodiment of a filtration device according to the invention.

Referring first to FIG. 1, the components of a first embodiment of a filtration device 10 are shown. The device 10 comprises four principal components/assemblies, namely an inlet funnel 11, a base container 13, a cell collection membrane 14 (with a support ring 15) and a fluid absorption assembly 19. In the assembled device 10, the cell collection membrane 14 and the fluid absorption assembly 19 are captivated between the inlet funnel 11 and the base container 13, as described below. The device has an overall height of approximately 10 cm.

The base container 13 is an open-topped cylindrical vessel. The inlet funnel 11 has the form of a hollow, tapered cylinder, which is open at both ends. A ring 111 is formed integrally with the lower (as viewed in the Figures) end of the inlet funnel 11 and forms a channel 112 between the wall of the inlet funnel 11 and the ring 111. The external surface of the rim of the base container 13 and the internal surface of the ring 111 are formed with cooperating screw-type formations 121,122, such that the inlet funnel 11 and the base container 13 may be engaged with a twist action when the rim of the base container 13 is inserted into the channel 112.

As noted above, the cell collection membrane 14 and the fluid absorption assembly 19 are captivated between the inlet funnel 11 and the base container 13.

The cell collection membrane 14 is circular and is ultrasonically welded to a rigid plastics support ring 15 to enable easy handling. The cell collection membrane 14 is porous, with a pore size small enough prevent the passage of cells of the type that are to be collected. Typically, the pore size is of the order of 1-2 μm.

The fluid absorption assembly 19 comprises a circular tray 192 to which is bonded, by ultrasonic welding, a retaining collar 191. The upper (as viewed in FIG. 1) end of the tray 192 is open, but is of reduced diameter, ie it is formed with an inwardly directed peripheral lip. The purpose of the lip is to retain within the assembly 19 a sponge 18, a sheet of superabsorbent material 17 and a cover membrane 16. Likewise, the upper end of the collar 191 is open, and receives the cell collection membrane 14 and its supporting ring 15. The base of the tray 192 is formed as a grid, with openings to permit the passage of fluid.

As the top of the fluid absorption assembly 19 is open, the cover membrane 16 is in direct contact with the underside of the cell collection membrane 14. The cover membrane 16 is also porous, with a pore size sufficient to allow the unrestricted flow of fluid. The pore size of the cover membrane 16 is therefore generally considerably greater than the pore size of the cell collection membrane 14, and may typically be about 100 μm-2 mm. Indeed, the cover membrane may alternatively take the form of a woven or other form of mesh or scrim.

The sheet of superabsorbent material 17 comprises particles of sodium polyacrylate polymer encapsulated between two layers of carrier material, such as tissue paper. A suitable material is Gelok® 14040S/S manufactured by Gelok International Corporation.

The sponge 18 is a body of soft, open-celled foam. The purpose of the sponge 18 is simply to act in the manner of a compression spring, pressing the sheet of superabsorbent material 17 and the cover membrane 16 towards the cell collection membrane 14.

Figure 2:
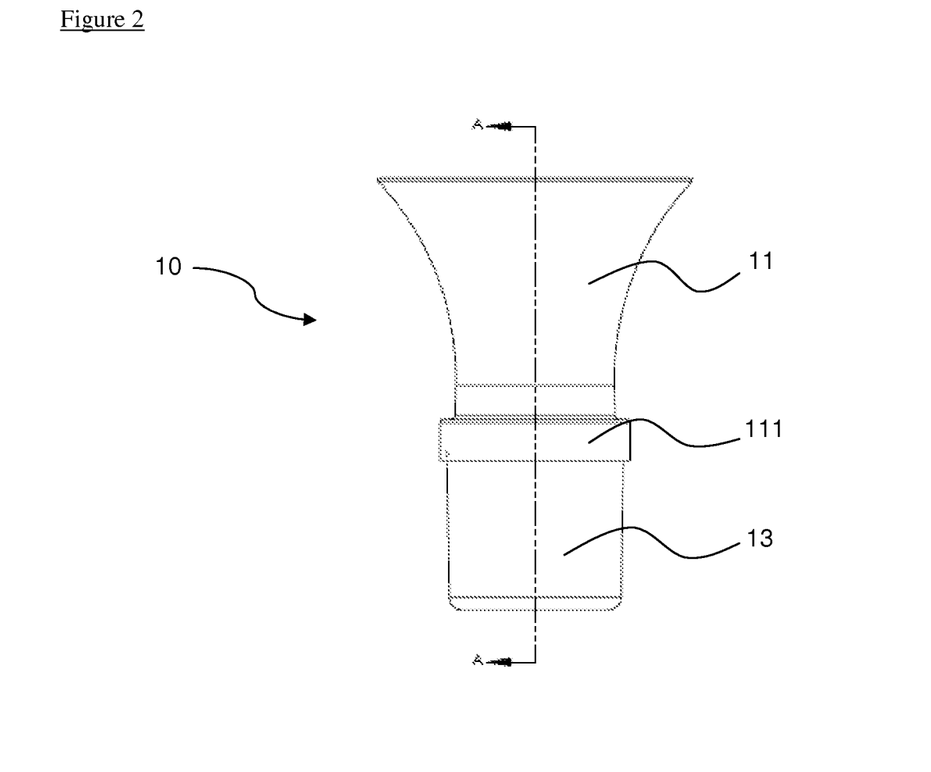
FIG. 2 shows a side view of the filtration device of FIG. 1.
Figure 3:
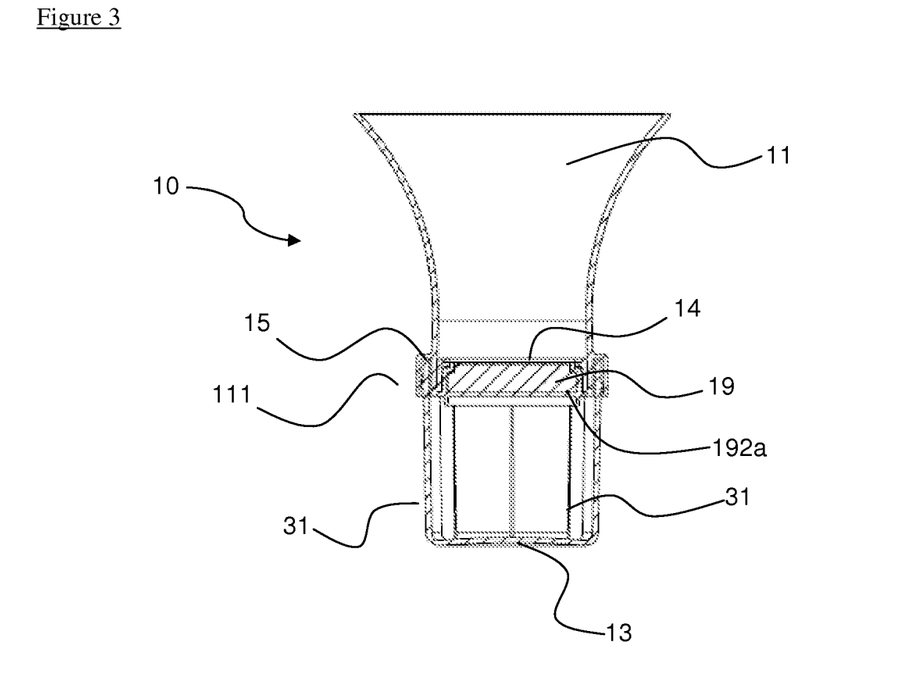
FIG. 3 shows a cross-sectional view of the filtration device of FIG. 2, along the line A-A.

The assembled device can be seen in FIGS. 2 and 3. As can be seen in FIG. 3, the tray 192 of the fluid absorption assembly 19 is formed with an integral flange 192a (most clearly seen in FIG. 1) that is seated on longitudinal ribs 31 (see FIG. 3) formed on the internal surface of the base container 13. Engagement of the inlet funnel 11 with the base container 13 causes the flange 192a to be captivated between the wall of the inlet funnel 11 and the ribs 31, thereby holding the fluid absorption assembly 19 in a fixed position. The cell collection membrane 14, with its supporting plastics ring 15, covers the open upper end of the fluid absorption assembly 19.

The filtration device 10 is supplied in its fully assembled configuration, as shown in FIGS. 2 and 3. In order to collect cellular material using the device, a fluid sample, eg a urine sample, is introduced into the inlet funnel 11, onto the porous cell collection membrane 14. Fluid is drawn through the cell collection membrane 14 and the cover membrane 16 both by gravity and by the action of the layer of superabsorbent material 17. The proximity of, and contact between, the cell collection membrane 14, the cover membrane 16 and the sheet of superabsorbent material 17 aids in drawing fluid through the cell collection membrane 14 and into the sheet of superabsorbent material 17. As the sheet of superabsorbent material 17 absorbs fluid, it expands. The soft foam material of the sponge 18 is compressed by the expanding superabsorbent material 17, thus allowing the expansion of the superabsorbent material 17 to be accommodated within the fluid absorption assembly 19 whilst still pressing the layer of superabsorbent material 17 and cover membrane 16 against the cell collection membrane 14. Excess fluid passes through the sheet of superabsorbent material 17 and the sponge 18, and is collected in the base container 13.

Due to the small pore size of the cell collection membrane 14, as fluid is drawn through the cell collection membrane 14 cellular material from the fluid sample is retained on its upstream surface. The device 10 may be left until all fluid has been drawn through the cell collection membrane 14. Alternatively, after a predetermined time any excess fluid remaining in the inlet funnel 11 may simply be tipped away.

The inlet funnel 11 and base container 13 are then separated by a simple twisting action. This enables the cell collection membrane 14, with its supporting ring 15, to be removed. The cell collection membrane 14 may then be transferred to, for instance, an optical microscope for analysis. The remaining components of the device 10, ie the base container 13, the fluid absorption assembly 19 and the inlet funnel 11 may be discarded, along with their contents.

Figure 4:
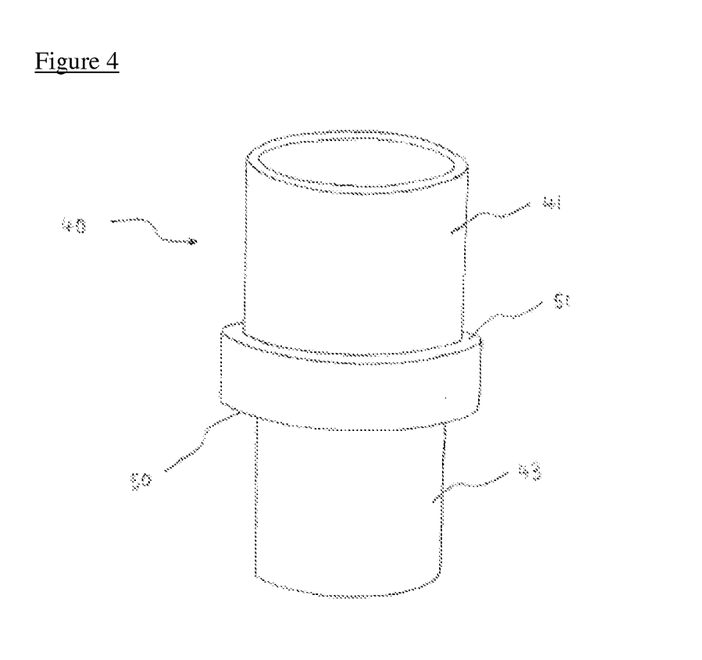
FIG. 4 is a perspective view of a second embodiment of a filtration device according to the invention.
Figure 5:
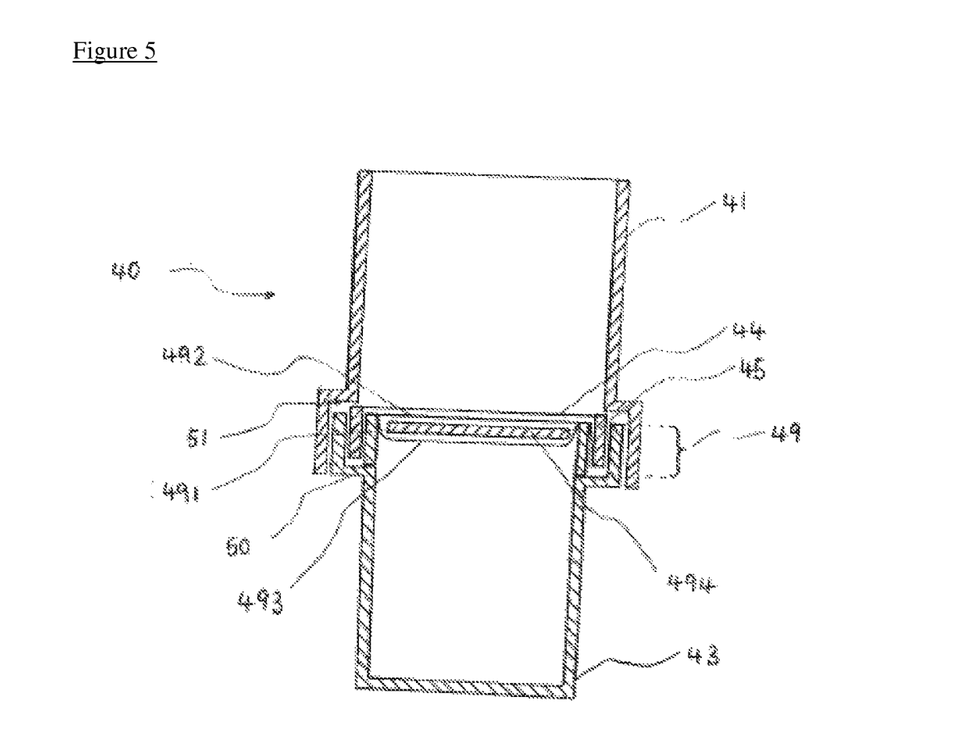
FIG. 5 shows a cross-sectional view of the filtration device of FIG. 4.
Figure 6:
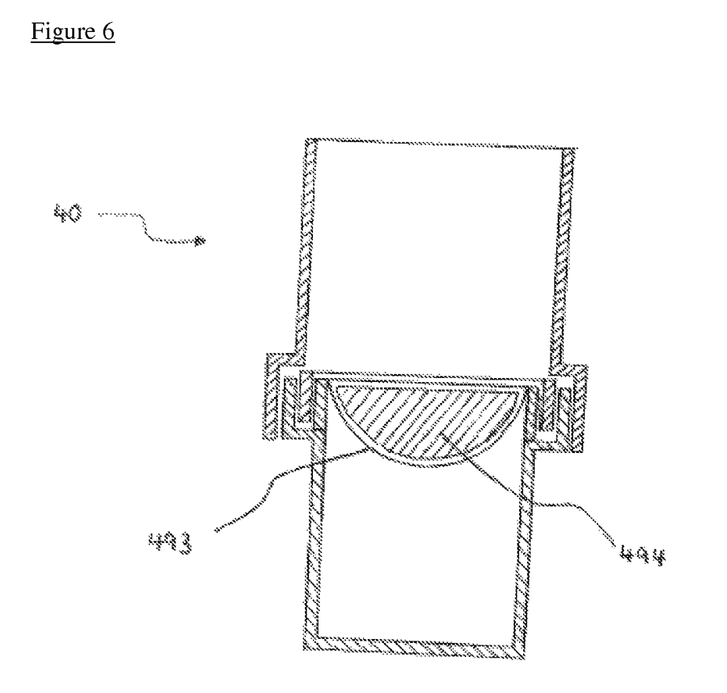
FIG. 6 shows a cross-sectional view of the filtration device of FIG. 4 where the absorbent material of the fluid absorption assembly has expanded on absorption of fluid.

Referring now to FIGS. 4 to 6, a second embodiment of a filtration device 40 is shown. As for the first embodiment, the device 40 comprises four principal components/assemblies, namely an open topped inlet cylinder 41, a base container 43, a cell collection membrane 44 (with a support ring 45) and a fluid absorption assembly 49. In the assembled device 40, the cell collection membrane 44 and the fluid absorption assembly 49 are captivated between the inlet cylinder 41 and the base container 43, as described below. The device has an overall height of approximately 10 cm.

The base container 43 is an open-topped cylindrical vessel. The inlet cylinder 41 has the form of a hollow cylinder, which is open at both ends. The external surface of the rim of the base container 43 and the internal surface of the rim of the inlet cylinder 41 are formed with cooperating screw-type formations such that the inlet cylinder 41 and the base container 43 may be engaged with a twist action when the rim of the base container 43 is inserted into the rim of the inlet cylinder 41.

As noted above, the cell collection membrane 44 and the fluid absorption assembly 49 are captivated between the inlet cylinder 41 and the base container 43.

The cell collection membrane 44 is circular and is ultrasonically welded to a rigid plastics support ring 45 to enable easy handling. The cell collection membrane 44 is porous, with a pore size small enough prevent the passage of cells of the type that are to be collected. Typically, the pore size is of the order of 0.1-2 µm.

To the extent so far described, the second embodiment is similar to the first. The second embodiment differs from the first in the nature of the fluid absorption assembly 49.

Figure 7:
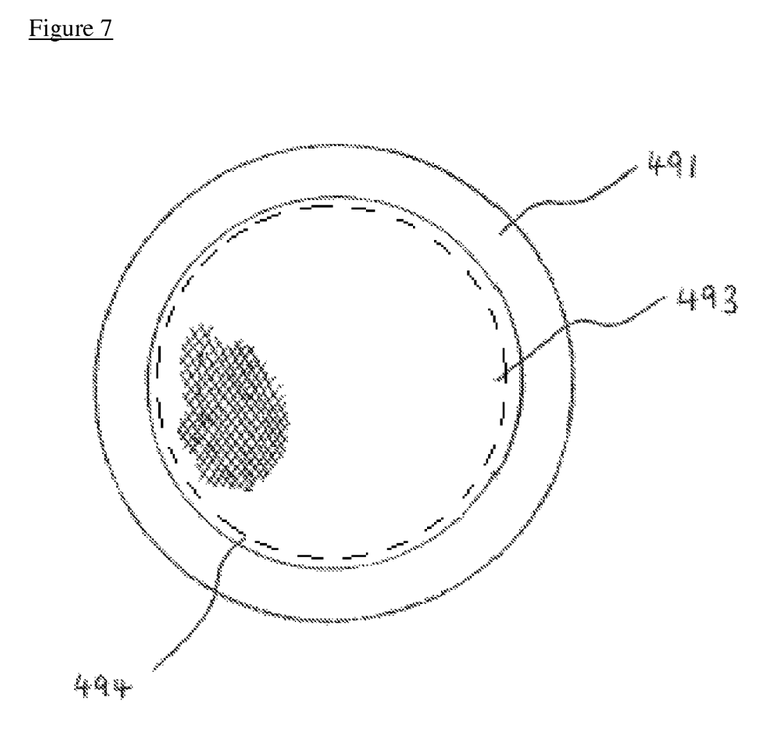
FIG. 7 shows an underside view of the fluid absorption assembly of the filtration device of FIG. 4.

The fluid absorption assembly 49 is circular and comprises a plastic ring 491 which is ultrasonically bonded to a circular cover membrane 492 and a sheet of a circular knitted material 493. The cover membrane 492 forms the upper (as viewed in FIG. 5) surface of the fluid absorption assembly 49, the sheet of circular knitted material 493 being located beneath (as viewed in the Figures, and in use) the cover membrane 492. Encapsulated between the cover membrane 492 and the circular knitted material 493 is a sheet of superabsorbent material 494. The circular knitted material 493 as viewed from below in FIG. 7 can be seen covering the pad of superabsorbent material 494 (the outline of which is shown in broken lines, as hidden detail) and surrounded by the plastic ring 491.

The fluid absorption assembly 49 is of a smaller diameter than the plastic ring 45 to which the cell collection membrane 44 is bonded. When assembled, the fluid absorption assembly 49 fits closely inside the plastic ring 45 that is bonded to the cell collection membrane 44.

When assembled, the cover membrane 492 is in direct contact with the underside of the cell collection membrane 44. The cover membrane 492 is also porous, with a pore size sufficient to allow the unrestricted flow of fluid. The pore size of the cover membrane 492 is therefore generally considerably greater than the pore size of the cell collection membrane 44, eg 100 µm or more.

The sheet of superabsorbent material 494 comprises particles of sodium polyacrylate polymer encapsulated between two layers of carrier material, such as tissue paper. A suitable material is Gelok® 14040S/S manufactured by Gelok International Corporation.

The circular knitted material 493 is a single 78-denier nylon material. The purpose of the circular knitted material 493 is to expand evenly as the pad of superabsorbent material expands on absorption of fluid whilst also applying a gentle upward (as viewed in FIG. 5) pressure on the superabsorbent material 494, pressing the superabsorbent material 494 against the cover membrane 492, and thus towards the cell collection membrane 44.

As can be seen in FIG. 5, the fluid absorption assembly 49 and the cell collection membrane 44 and its plastic ring 45 are seated on a flange 50 formed at the rim of the base container 43. Engagement of the inlet cylinder 41 with the base container 43 causes the fluid absorption assembly 49 and cell collection membrane 44 and its support ring 45 to be captivated between the flange 50 and a corresponding surface 51 of the inlet cylinder 41, thereby holding the fluid absorption assembly 49 and cell collection membrane in a fixed position.

The filtration device 40 is supplied in its fully assembled configuration, as shown in FIGS. 4, 5 and 6. In order to collect cells using the device, a fluid sample, eg a urine sample, is introduced into the inlet cylinder 41, onto the porous cell collection membrane 44. Fluid is drawn through the cell collection membrane 44 and the cover membrane 492 both by gravity and by the action of the superabsorbent material 494. The proximity of, and contact between, the cell collection membrane 44, the cover membrane 492 and the superabsorbent material 494 aids in drawing fluid through the cell collection membrane 44 and into the superabsorbent material 494. As the superabsorbent material 494 absorbs fluid, it expands. The circular knitted material 493 is able to expand evenly in all directions as the superabsorbent material 494 expands, thus allowing the expansion of the superabsorbent material 494 to be accommodated within the fluid absorption assembly 49. The circular knitted material 493 is sufficiently elastic to apply a gentle upward pressure to the superabsorbent material 494, pressing the superabsorbent material 494 and cover membrane 492 against the cell collection membrane 44. Excess fluid passes through the superabsorbent material 494 and the circular knitted material 493, and is collected in the base container 43.

The use of the circular knitted material 493 rather than the sponge assembly of device 10 allows for a greater volume of fluid to be used, as fluid can pass more easily through the fluid absorption assembly 49 and into the base container 43. This prevents blockage of the device 40 when larger volumes of fluid are used.

Due to the small pore size of the cell collection membrane 44, as fluid is drawn through the cell collection membrane 44, cells from the fluid sample are retained on its upstream surface. The device 40 may be left until all fluid has been drawn through the cell collection membrane 44. Alternatively, after a predetermined time any excess fluid remaining in the inlet cylinder 41 may simply be tipped away.

The inlet cylinder 41 and base container 43 are then separated by a simple twisting action. This enables the cell collection membrane 44, with its supporting ring 45, to be removed. The cell collection membrane 44 may then be transferred to, for instance, an optical microscope for analysis. The remaining components of the device 40, ie the base container 43, the fluid absorption assembly 49 and the inlet cylinder 41 may be discarded, along with their contents.

The invention claimed is:

1. A device for collecting cellular material from a fluid sample, the device comprising:
   a) first and second chambers that are releasably connected to each other at cooperating ends and which define a fluid flow path from the first chamber to the second chamber, a first chamber having an open free end;
   b) a porous membrane captivated where the cooperating ends of the first and second chambers are connected to each other, the porous membrane being positioned in the fluid flow path and having upstream and downstream surfaces and being removable from between the first and second chambers when the first and second chambers are disconnected from each other;
   c) an absorbent body positioned adjacent to the downstream surface of the porous membrane; and
   d) a resilient member arranged to urge the absorbent body towards the porous membrane, the resilient member separated from a closed end of the second chamber by a space configured to collect fluid, the open free end of the first chamber being at an opposite end of the device from the closed end of the second chamber;
   wherein, in use, the first chamber remains open at the open free end and a sample introduced into the first chamber contacts the upstream surface of the porous membrane and fluid is drawn through the porous membrane and is absorbed by the absorbent body, cellular material present in the sample being retained upon the upstream surface of the porous membrane,
   wherein, after separation of the first and second chambers, the porous membrane can be removed from the device for analysis of cellular material deposited on the upstream surface thereof, and
   wherein the absorbent body comprises a superabsorbent material.

2. The device of claim 1, wherein the absorbent body is positioned where the first and second chambers are connected to each other.

3. The device of claim 1, wherein the first chamber and a second chamber are connectable together by means of a screw-type fitting.

4. The device of claim 1, wherein the resilient member comprises a compressible body.

5. The device of claim 4, wherein the compressible body is located beneath the absorbent body.

6. The device of claim 4, wherein the compressible body is an open-celled plastics foam.

7. The device of claim 1, wherein the resilient member comprises a sheet of material having a degree of elasticity, such that the sheet of material is sufficiently deformable to accommodate the swelling of the absorbent body whilst having sufficient resistance to apply upward pressure to the absorbent body.

8. The device of claim 7, wherein the sheet of material is capable of stretching equally in all directions and is sufficiently porous to allow excess fluid to pass through it.

9. The device of claim 7, wherein the sheet of material is a circular knitted material.

10. The device of claim 1, wherein the superabsorbent material is sodium polyacrylate polymer.

11. The device of claim 10, wherein the sodium polyacrylate polymer is incorporated into a sheet in the form of particles encapsulated between two layers of carrier material.

12. The device of claim 11, wherein the carrier material is tissue paper.

13. The device of claim 1, wherein the second chamber has a volume of between about 10 and 250 ml.

14. The device of claim 1, wherein the porous membrane is a membrane filter.

15. The device of claim 1, wherein the porous membrane is a polycarbonate membrane.

16. The device of claim 1, wherein the porous membrane has an average pore size of between about 0.1 and 5 µm.

17. The device of claim 1, wherein the porous membrane is retained within a rigid frame.

18. The device of claim 1, wherein the absorbent body is in direct contact with the downstream surface of the porous membrane.

19. The device of claim 1, wherein a porous intermediate component is interposed between the absorbent body and the porous membrane.

20. The device of claim 1, wherein the absorbent body is housed within a rigid holder that is secured by one or both of the first and second chambers.

21. The device of claim 20, wherein the rigid holder further houses a fluid-transmissive cover.

22. The device of claim 1, which is disposable and is intended to be discarded after a single use.

23. The device of claim 1, wherein the fluid sample is selected from the group consisting of a biological sample, a food or drink sample, a pharmaceutical sample, a pharmaceutical cell culture, a water sample, a wastewater sample, a potable water sample, a cosmetics sample, or other fluid sample taken for the purposes of environmental control and monitoring.

24. The device of claim 23, wherein the fluid sample is a biological fluid sample.

25. A method for collecting and analysing cellular material from a fluid sample, the method comprising:
   i) providing a device comprising:
      a) first and second chambers that are releasably connected to each other at cooperating ends and which define a fluid flow path from the first chamber to the second chamber, the first chamber having an open free end;
      b) a porous membrane captivated where the cooperating ends of the first and second chambers are connected to each other, the porous membrane being positioned in the fluid flow path and having an upstream surface and a downstream surface and being removable from between the first and second chambers when the first and second chambers are disconnected from each other;
      c) an absorbent body positioned adjacent to the downstream surface of the porous membrane; and d) a resilient member arranged to urge the absorbent body towards the porous membrane, the resilient member separated from a closed end of the second chamber by a space configured to collect fluid, the open free end of the first chamber being at an opposite end of the device from the closed end of the second chamber;

wherein, in use, the open free end of the first chamber remains open and a sample introduced into the first chamber contacts the upstream surface of the porous membrane and fluid is drawn through the porous membrane and is absorbed by the absorbent body, cellular material present in the sample being retained upon the upstream surface of the porous membrane, wherein, after separation of the first and second chambers, the porous membrane can be removed from the device for analysis of cellular material deposited on the upstream surface thereof, and wherein the absorbent body comprises a superabsorbent material;

ii) introducing a fluid sample into said device, such that the sample is in contact with the upstream surface of the porous membrane and the absorbent body urges the fluid sample through and downstream of the porous membrane; and iii) subsequently removing the porous membrane from between the first chamber and the second chamber when the first and second chambers are disconnected, for analysis of the cellular material deposited on its upstream surface.

26. The method of claim 25, wherein the fluid sample is a biological sample.

27. The method of claim 26, wherein the biological sample is selected from the group consisting of whole blood, plasma, serum, cerebrospinal fluid, urine, bile, faeces, mucus, amniotic fluid, lymph, pericardial fluid, saliva and synovial fluid.

28. The method of claim 25, wherein the wherein the fluid sample is selected from the group consisting of a food or drink sample, a pharmaceutical sample, a pharmaceutical cell culture, a water sample, a wastewater sample, a potable water sample, a cosmetics sample, or other fluid sample taken for the purposes of environmental control and monitoring.

29. The device of claim 1, wherein the resilient member is captivated where the cooperating ends of the first chamber and the second chamber are connected.

30. The device of claim 1, further comprising:
a support held in a fixed position where the first and second chambers are connected to each other, wherein the resilient member and the absorbent body are supported between the first and second chambers by the support.

31. The device of claim 1, wherein the resilient member is a knitted material supported on a frame, the absorbent body supported by the knitted material and the frame supported where the first and second chambers connect, the knitted material configured to expand as the absorbent body absorbs fluid.

32. A device for collecting cellular material from a fluid sample, the device comprising:
a) a first chamber having a first open end and a second open end opposite the first open end, and a second chamber having an open attachment end and a closed end opposite the open attachment end, wherein first and second chambers are releasably connected at the second open end of the first chamber and the openfirst attachment end of the second chamber to form an engagement section between the first and second chambers which defines a fluid flow path from the first chamber to the second chamber;
b) a porous membrane captivated at the engagement section between the first and second chambers when the first and second chambers are connected to each other, the porous membrane being positioned in the fluid flow path and having upstream and downstream surfaces and being removable from between the first chamber and the second chamber when the first chamber and the second chamber are disconnected from each other;
c) an absorbent body comprising a superabsorbent material positioned adjacent to the downstream surface of the porous membrane;
d) a resilient member arranged to urge the absorbent body towards the porous membrane; and
e) a support that supports the resilient member in a position proximate the engagement section with a space between the resilient member and the closed end of the second chamber.

* * * * *